(12) United States Patent
Gabetta et al.

(10) Patent No.: US 7,232,916 B1
(45) Date of Patent: Jun. 19, 2007

(54) PROCESS FOR THE PREPARATION OF A TAXANE DERIVATIVE

(75) Inventors: Bruno Gabetta, Milan (IT); Daniele Ciceri, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 11/432,866

(22) Filed: May 11, 2006

(51) Int. Cl.
*C07D 317/70* (2006.01)
*C07D 407/02* (2006.01)
*C07D 493/12* (2006.01)

(52) U.S. Cl. ...................................... 549/296; 549/297

(58) Field of Classification Search ............... None
See application file for complete search history.

(56) References Cited

U.S. PATENT DOCUMENTS 6,737,534 B2    5/2004  Pontiroli et al. ............ 549/296

6,906,101 B1 *  6/2005  Bombardelli et al. ....... 514/463

FOREIGN PATENT DOCUMENTS

WO    WO 01/02407 A2    1/2001

* cited by examiner

*Primary Examiner*—D. Margaret Seaman
*Assistant Examiner*—Nizal S. Chandrakumar
(74) *Attorney, Agent, or Firm*—Mathews, Shepherd, McKay & Bruneau, P.A.

(57) ABSTRACT

The invention relates to an improved process for the synthesis of 13-(N-Boc-β-isobutylserinyl)-14-β-hydroxybaccatin III-1,14-carbonate (I), wherein carbonation of the 1,14-hydroxy groups of the baccatin skeleton is carried out with bis(trichloromethylcarbonate and the 7-hydroxy group is protected with a trichloroacetyl group.

3 Claims, No Drawings

PROCESS FOR THE PREPARATION OF A TAXANE DERIVATIVE

FIELD OF THE INVENTION

The present invention relates to taxane derivatives, in particular to a process for the preparation of 13-(N-Boc-β-isobutylserinyl)-14-β-hydroxybaccatin III-1,14-carbonate (I):

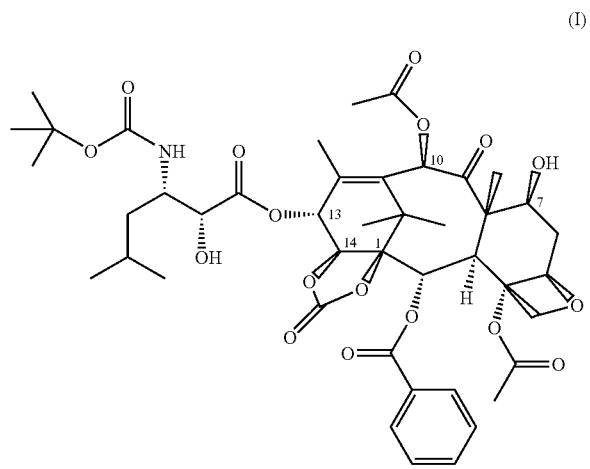

BACKGROUND OF THE INVENTION

Compound (I), disclosed for the first time in WO 01/02407, is particularly active against breast, lung, ovary, colon, prostate, kidney and pancreas tumours, also in case of resistance to known antitumour agents such as adriamycin, vinblastine and some Pt derivatives.

A number of synthetic methods for the preparation of (I), which comprise the use of an oxazolidine-protected side chain, are reported in the literature. In U.S. Pat. No. 6,737,534 10-deacetylbaccatin III, a starting material easily available from *Taxus baccata* leaves, is first protected at the 7- and 10-positions, oxidised at the 13-position and then hydroxylated at the 14-position. Thereafter, carbonation of the vicinal-1,14 hydroxy groups to give the 1,14-carbonate derivative is carried out with phosgene, followed by reduction of the 13-keto group to hydroxy group and removal of the protecting groups from the 7- and 10-positions, to obtain 10-deacetyl-14β-hydroxybaccatin III-1,14 carbonate, which is selectively acetylated at the 10-hydroxy group, converted into the 7-triethylsilyl derivative and reacted with (4S,5R)-N-Boc-2-(2,4-dimethoxyphenyl)-4-isobutyl-1-oxazolidine-5-carboxylic acid. Removal of the triethylsilyl and dimethoxybenzylidene protecting groups affords compound (I).

WO 01/02407 discloses two synthetic routes to compound (I), both starting from 14β-hydroxy-10-deacetylbaccatin III, a constituent of *Taxus wallichiana* leaves. The first, referred to as process (A), comprises the following steps:

(a) conversion of 14β-hydroxy-10-deacetylbaccatin III into the 7-triethylsilyl derivative;
(b) carbonation of the 1,14 hydroxy groups;
(c) acetylation of the 10-hydroxy group;
(d) reaction of the product of step (c) with (4S,5R)-N-Boc-2-(2,4-dimethoxyphenyl)-4-isobutyl-1-oxazolidine-5-carboxylic acid;
(e) cleavage of the triethylsilyl and dimethoxybenzylidene groups from the product of step (d);

The second one, referred to as process (B), comprises the following steps:

(a') acetylation of the 10-hydroxy group of 14β-hydroxy-10-deacetylbaccatin III;
(b') carbonation of the 1,14 hydroxy groups;
(c') silylation of the 7-hydroxy group;
(d') reaction of the product from step (c') with (4S,5R)-N-Boc-2-(2,4-dimethoxyphenyl)-4-isobutyl-1-oxazolidine-5-carboxylic acid;
(e') cleavage of the triethylsilyl and dimethoxybenzylidene groups from the product of step (d').

In process B, carrying out acetylation of the 10-hydroxy group before protecting the 7-position allows to avoid the formation of a mixture of regioisomers at the 7- and 10-positions, which always occurs in process A, where acetylation is carried out after protection of the 7-hydroxy group. Therefore, process B is advantageous over process A in that it is highly regioselective. However, scaling up process B to a multi-kilo scale is troublesome, because, for the sake of safety, large amounts of phosgene cannot be loaded into a reactor, thus step (b') cannot be carried out by adding 14β-hydroxy-10-deacetylbaccatin III to phosgene. If phosgene is instead bubbled into a solution of 14β-hydroxy-10-deacetylbaccatin III, a relevant amount (about 7%) of impurity (II) forms.

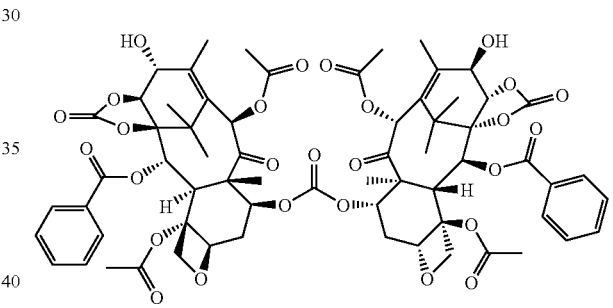

Formation of (II) is due to the fact that also the 7-hydroxy group is reactive to phosgene, giving rise to compound (III).

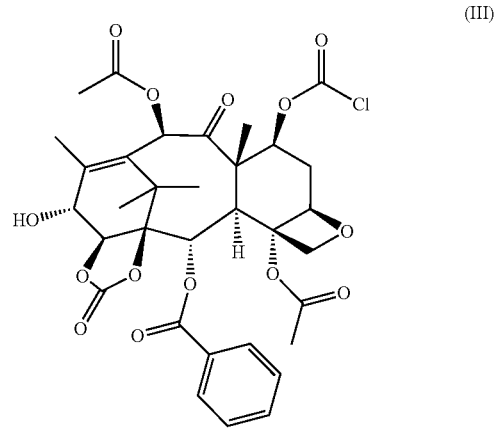

Thus, when carbonation is carried out on a large scale and phosgene is bubbled into the reactor, compound (III) reacts with 14β-hydroxy-10-deacetyl baccatin III, leading to (II).

This impurity also forms when process (B) is carried out on a smaller scale, but in amounts lower than 0.4%.

Due to the close structure similarity with 14β-hydroxy-baccatin III-1,14 carbonate, compound (II) can be removed only through column chromatography, thus lowering the yield and increasing the cost of the process, especially on an industrial scale.

A further drawback of process B lies in the fact that triethylsilyl fluoride which forms after removal of the TES group cannot be completely removed by crystallisation and low-pressure column chromatography is necessary to obtain a final product complying with the purity requirements of pharmaceutical products. However, it is well known that on an industrial scale low-pressure column chromatography is troublesome, expensive and poses problems with the handling and destruction of silica contaminated with toxic materials.

DESCRIPTION OF THE INVENTION

It has now been found that the above-mentioned drawbacks can be overcome by carrying out step (b') with bis(trichloromethyl)carbonate instead of phosgene and carrying out step (c') with trichloroacetylchloride instead of triethylsilylchloride.

Accordingly, the invention relates to a process for the preparation of a compound of formula (I)

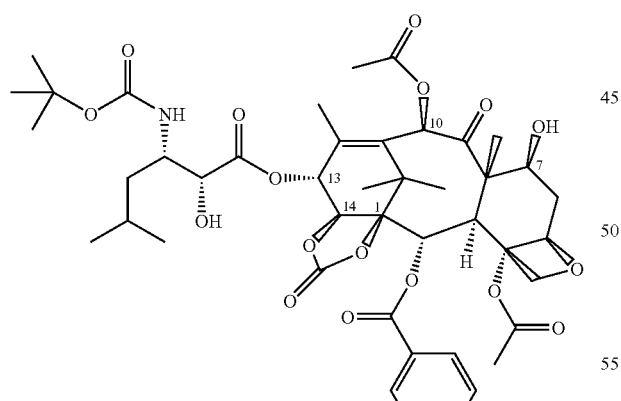
(I)

which comprises the following steps:

a) acetylation of the 10-hydroxy group of 14β-hydroxy-10-desacetylbaccatin III (IV)

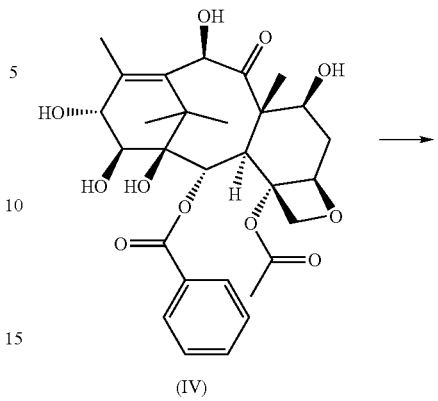
(IV)

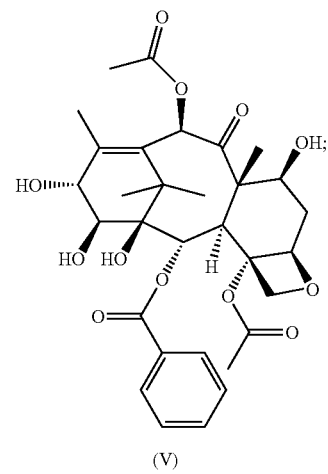
(V)

b) reaction of (V) with bis(trichloromethyl)carbonate to afford the 1,14 carbonate derivative (VI)

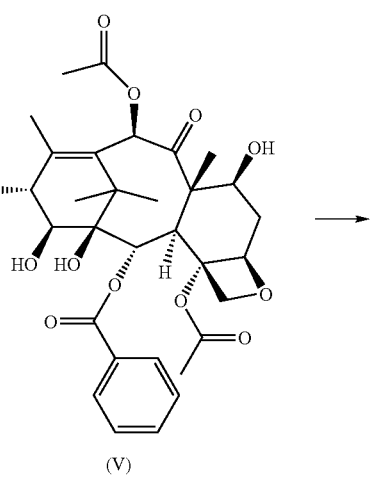
(V)

-continued
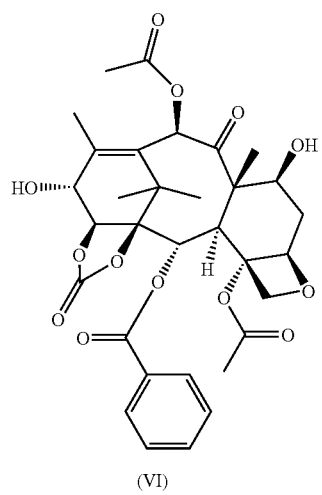
(VI)
c) reaction of (VI) with trichloroacetyl chloride to afford (VII)
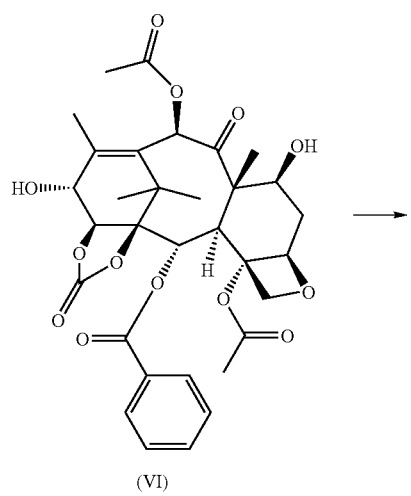
(VI)
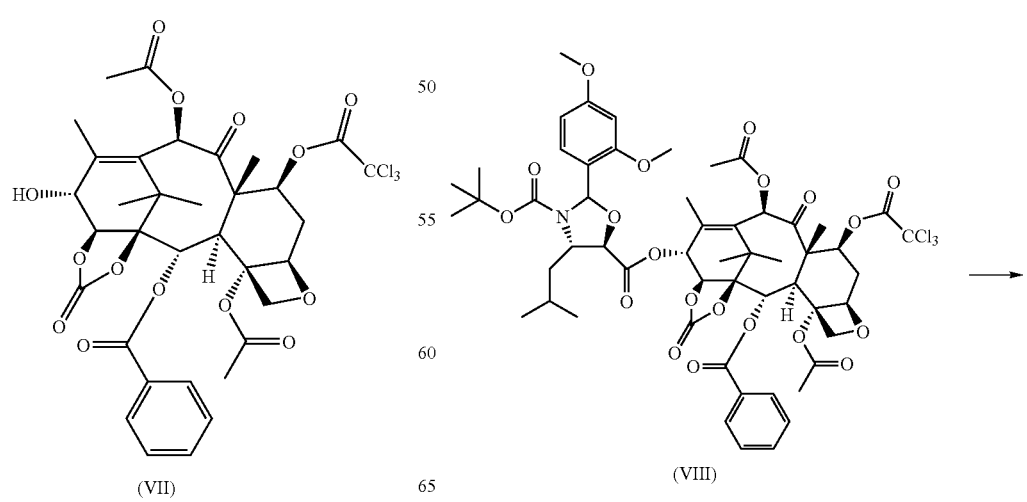
(VII)
d) reaction (VII) with (4S,5R)-N-Boc-2-(2,4-dimethoxyphenyl)-4-isobutyl-1-oxazolidine-5-carboxylic acid, to afford (VIII)
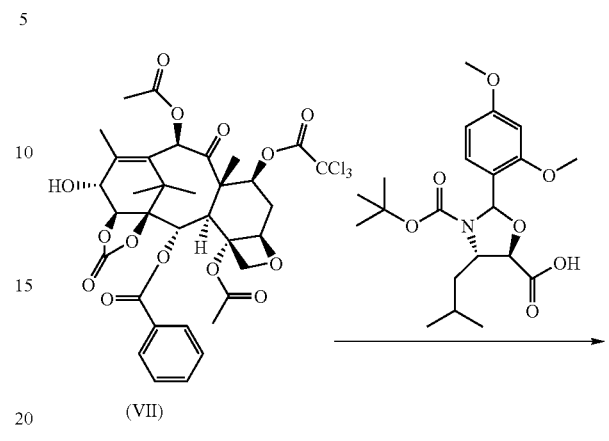
(VII)
(VIII)
e) removal of the protective trichloroacetyl group with alkaly, preferably ammonium hydroxide, from compound (VIII)
(VIII)

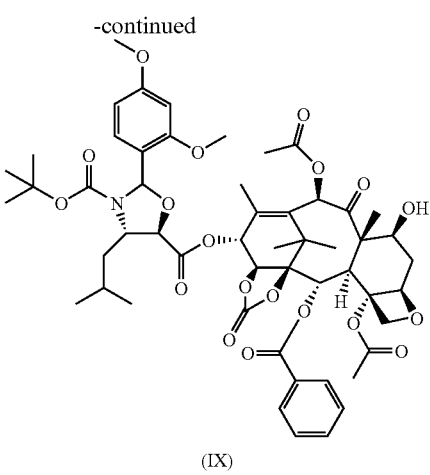

(IX)

f) removal of the dimethoxybenzylidene protective group from compound (IX)

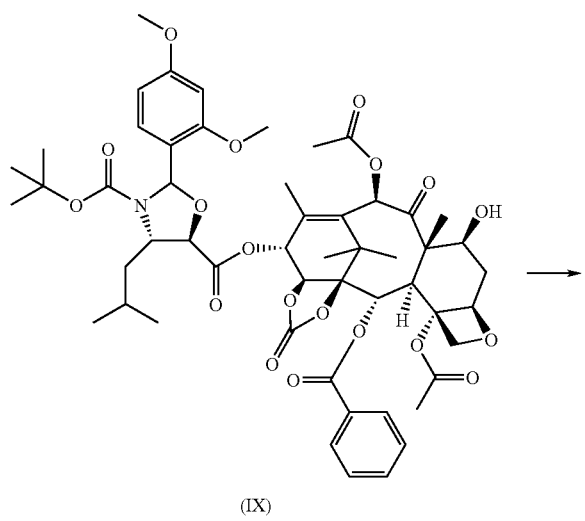

(IX)

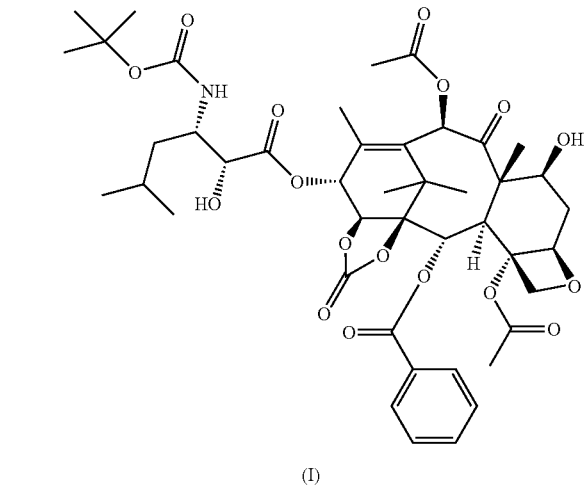

(I)

According to a preferred embodiment of the invention, acetylation of the 10-position (step a) is carried out with acetic anhydride in the presence of cerium, scandium, or ytterbium salts, preferably $CeCl_3 \times 7H_2O$. Step b) is carried out with bis(trichloromethyl)carbonate in dichloromethane at 0° C. in the presence of a base preferably pyridine. Step c is carried out using trichloroacetylchloride in a suitable solvent, such as dichloromethane in the presence of a base preferably pyridine at −10° C. (4S,5R)-N-Boc-2-(2,4-dimethoxyphenyl)-4-isobutyl-1-oxazolidine-5-carboxylic acid for use in step (d') can be prepared as described in WO 01/02407. Step d) is carried out in an anhydrous apolar solvent, preferably dichloromethane, in the presence of a base, preferably 4-dimethylaminopyridine (DMAP) and of a condensing agent, such as dicyclohexylcarbodiimide (DCC), yielding a product which, after crystallization, has a purity higher than 98.5%. The trichloroacetyl group at the 7-position can be removed with ammonium hydroxide in an aprotic dipolar solvent such as acetonitrile or N-methylpyrrolidone and isolated through precipitation in water to give a product with purity of not less than 98.5%. Finally, the product of step e) is treated with methanolic HCl. Compound (I) is then crystallized from ethyl acetate and subsequently from acetone/hexane to afford a solid with a purity of not less than 99.9%.

Therefore, the use of bis(trichloromethyl)carbonate in step b) is advantageous in that it prevents formation of impurity (II). The use of trichloroacetyl chloride as a protective group in intermediate (VII) allows to obtain a compound of formula (VIII), which easily crystallizes from methanol with a purity higher than 98.5%, whereas the 7-triethylsilyl analogue failed to crystallize from different solvents. More important, trichloroacetamide which forms following deprotection of the 7-position is effectively removed from compound (IX) by treatment with ammonium hydroxide, due to its solubility in a mixture of water and either acetonitrile or N-methylpyrrolidone. Thus, after cleavage of the dimethoxybenzylidene group and crystallisation, compound (I) is obtained with a purity of not less than 99.9%.

The following examples illustrate the invention in greater detail.

EXAMPLES

Example 1

14β-Hydroxybaccatin III (V) (step a)

14β-Hydroxy-10-deacetylbaccatin III (VII) (10 kg) was suspended in THF (45 L) and $CeCl_3 \times 7H_2O$ (0.5 kg) was added. Acetic anhydride (6.6 kg) was added over 20 minutes and the reaction mixture was stirred at room temperature for 2 hours, then quenched by addition of water (10 L). THF was distilled off under vacuum and the residue was dried until the water content was less than 10%, then crystallized from ethyl acetate to afford the title compound as a white solid (8.2 kg, yield 85%).

$^1$H-NMR (300 MHz, $CDCl_3$): 1.02 (s, 3H), 1.08 (s, 3H), 1.62 (s, 3H), 1.78 (ddd, 1H), 1.99 (d, 3H), 2.16 (s, 3H), 2.24 (s, 3H), 2.46 (ddd, 1H), 3.43 (OH, s), 3.73 (d, 1H), 3.89 (d, 1H), 4.18 (s, 2H), 4.35 (dd, 1H), 4.60 (dd, 1H), 4.91 (dd, 1H), 5.73 (d, 1H), 6.28 (s, 1H), 7.39 (t, 1H), 7.52 (dt, 2H), 8.06 (d, 2H).

Example 2

14β-Hydroxybaccatin III-1,14-carbonate (VI) (step b)

14β-Hydroxybaccatin III (VIII) (5.0 kg) was dissolved in a mixture of dichloromethane (48.0 L) and pyridine (8.0 kg). The reaction mixture was cooled down to −10° C. and a solution of bis(trichloromethylcarbonate) (5.4 kg) in dichloromethane (32.0 L) was added over 30 minutes. The reaction was quenched by addition of a sodium carbonate solution (11.9 kg) dissolved in water (55.0 L) and the resulting biphasic mixture was stirred for 1 hour, then diluted with water. The phases were separated and the aqueous one was extracted with dichloromethane (23.8 L). The organic phases were pooled and washed with 20% hydrochloric acid (40 L), then with water (30.0 L) and with brine (40 L). Part of the solvent was distilled off under vacuum and the solution of the title compound (VI) was used directly in the next step.

$^1$H-NMR (300 MHz, CDCl$_3$): 1.24 (s, 3H), 1.28 (s, 3H), 1.56 (OH, s), 1.75 (s, 3H), 1.92 (ddd, 1H), 2.13 (d, 3H), 2.60 (ddd, 1H), 2.28 (s, 3H), 2.34 (s, 3H), 2.82 (OH, 1H), 3.76 (d, 1H), 4.25 (d, 1H), 4.34 (d, 1H), 4.46 (dd, 1H), 4.83 (d, 1H), 5.01 (dd, 1H), 5.09 (d, 1H), 6.12 (d, 1H), 6.34 (s, 1H), 7.29 (t, 1H), 7.52 (t, 2H), 8.06 (d, 2H).

Example 3

7-Trichloroacetyl-14-hydroxybaccatin III-1,14 carbonate (VII) (step c)

The solution from the previous step was added with pyridine (2 L) and cooled down to −10° C. Trichloroacetyl chloride (1.6 kg) was added over 15 minutes maintaining the temperature between −10 and 0° C. The reaction mixture was stirred at the same temperature for 2 hours. The reaction was quenched by addition of a solution of NaHSO$_4$ (2 kg) in water (20 L). The phases were separated and the aqueous one was extracted with dichloromethane (2 L). The combined organic phases were evaporated to small volume and toluene (20 L) was added. The solvent was removed by distillation at atmospheric pressure until the distillation-head reached a temperature of 110° C. On cooling the title compound crystallised as a white solid, which was filtered off and dried under vacuum. (4.96 kg, yield of two steps 85%).

$^1$H-NMR (300 MHz, CDCl$_3$): 1.20 (s, 3H), 1.28 (s, 3H), 1.93 (s, 3H), 2.03 (ddd, 1H), 2.17 (d, 3H), 2.20 (s, 3H), 2.38 (s, 3H), 2.71 (ddd, 1H), 3.02 (d, OH), 3.91 (d, 1H), 4.24 (d, 1H), 4.37 (d, 1H), 4.83 (d, 1H), 5.00 (dd, 1H), 5.04 (m, 1H), 5.71 (dd, 1H), 6.17 (d, 1H), 6.44 (s, 1H), 7.52 (t, 2H), 7.66 (t, 1H), 8.04 (d, 2H).

Example 4

(7-Trichloroacetyl)-13-(N-Boc-2-(2,4-dimethoxyphenyl)-4-isobutyl-5-oxazolydinyl)-14β-hydroxybaccatin-1,14-carbonate (VII) (step d)

7-Trichloroacetyl-14-hydroxybaccatin III-1,14 carbonate (IV) (4.96 kg) and dimethylamminopyridine (DMAP) (100 g) were added to a solution of (4S,5R)-N-Boc-(2,4-dimethoxyphenyl)-4-isobutyl-1-oxazolidine-5-carboxylic acid (4.0 kg) in dichloromethane (60 L). The reaction mixture was cooled down to 5° C. and added with a solution of dicyclohexylcarbodiimide (2.5 kg) in dichloromethane (18 L) over 30 minutes to give a white suspension which was stirred for 3 hours. DCU was filtered off and washed with dichloromethane (4 L). The resulting solution was washed in turn with a pH 3.5 phosphate buffer (100 L) and brine (50 L) and added with methanol, which brought about the crystallization of the title compound (VIII), which was dried under vacuum at 60° C. (yield: 6.9 kg, 92%).

$^1$H-NMR (300 MHz, CDCl$_3$): 1.10 (d, 6H), 1.33 (s, 2H), 1.37 (s, 2H), 1.37 (s, 9H), 1.60 (m, 1H), 1.95 (s, 3H), 1.97 (m, 2H), 2.04 (ddd, 1H), 2.16 (d, 3H), 2.20 (s, 3H), 2.34 (s, 3H), 2.68 (ddd, 1H), 3.85 (s, 3H), 3.95 (s, 3H), 4.26 8d, 1 h), 4.36 (d, 3H), 4.63 (m, 1H), 4.88 (d, 1H), 4.97 (dd, 1H), 5.76 (dd, 1H), 6.19 (d, 1H), 6.46 (s, 1H), 6.50 (t, 1H), 6.50 (d, 2H), 6.53 (dd, 1H), 7.27 (d, 1H), 7.49 (t, 1H), 7.64 (t, 2H), 8.03 (d, 2H).

Example 5

13-(N-Boc-2-(2,4-dimethoxyphenyl)-4-isobutyl-5-oxazolydinyl)-14β-hydroxybaccatin-1,14-carbonate (IX) (step e)

(7-Trichloroacetyl)-13-(N-Boc-2-(2,4-dimethoxyphenyl)-4-isobutyl-5-oxazolydinyl)-14β-hydroxybaccatin-1,14-carbonate (VIII) (6.9 kg) was dissolved in N-methylpyrrolidone (11 L). A solution of 2M ammonia in methanol (293 ml) was added to the reaction mixture over 10 minutes and stirred at room temperature for 45 minutes. The reaction mixture was added over 1 hour to water (110 L) and stirred for 30 minutes. The product was filtered off and washed with water (50 L). The title compound (IX) was dried at 60° C. under vacuum (6.14 kg, 99%).

$^1$H-NMR (300 MHz, CDCl$_3$):1.09 (d, 6H), 1.30 (s, 3H), 1.37 (s, 12H), 1.72 (s, 3H), 1.79 (m, 3H), 1.85 (m, 1H), 2.04 (d, 3H), 2.26 (s, 3H), 2.31 (s, 3H), 2.55 (m, 1H), 3.76 (d, 1H), 3.83 (s, 3H), 3.88 (s, 3H), 4.23 (d, 1H), 6.53 (m, 1H), 4.30 (d, 1H), 4.45 (dd, 1H), 4.85 (d, 1H), 4.95 (dd, 1H), 6.14 (d, 1H), 6.33 (s, 1H), 6.48 (m, 1H), 6.52 (m, 2H), 7.25 (m, 1H), 7.47 (t, 2H), 7.61 (t, 2H), 8.01 (d, 1H).

Example 6

13-(N-Boc-4-isobutyl-5-oxazolydinyl)-14β-hydroxybaccatin-1,14-carbonate (I) (step f)

13-(N-Boc-2-(2,4-dimethoxyphenyl)-4-isobutyl-5-oxazolydinyl)-14β-hydroxybaccatin-1,14-carbonate (IX) (6.1 kg) was dissolved in CH$_2$Cl$_2$ (20 L). The solution was cooled down to 0° C. and added dropwise at 0° C. with a solution of 0.5 M HCl in methanol (12 L) and the resulting mixture was stirred at room temperature for 4 hours.

The reaction mixture was poured into a vigorously stirred biphasic mixture of CH$_2$Cl$_2$ (27 L) and aqueous NaHCO$_3$ (0.6 kg in 21 L of water), keeping the pH between 6 and 7 during the addition. The organic phase was separated and the aqueous one was extracted twice with CH$_2$Cl$_2$ (2×2 L). The organic phase was evaporated to 18 L and EtOAc (18 L) was added and the solution reduced again to a volume of 18 L. The solution was left to crystallise overnight. The solid was filtered off and washed with EtOAc (7 L). The filtrate was dried overnight under vacuum at 40° C. (4.53 kg). The dry white solid was dissolved at 40° C. in acetone (20 L) and precipitated whit n-hexane (40 L). The mixture was left to crystallise at room temperature overnight. The product was filtered off, washed with n-hexane and dried under vacuum, to obtain 3.75 kg with 99.9% purity.

$^1$H-NMR (300 MHz, CDCl$_3$): 0.95 (d, 3H), 0.96 (d, 3H), 1.21 (m, 1H), 1.25 (s, 1.32 (s, 3H), 1.35 (s, 9H), 1.43 (m, 1H), 1.65 (m, 1H), 1.69 (s, 3H), 1.86 (m, 1H), (d, 3H), 2.22 (s, 3H), 2.40 (s, 3H), 2.52 (ddd, 1H), 3.68 (d, 1H), 4.08 (m, 1H), (d, 1H), 4.27 (d, 1H), 4.30 (dd, 1H), 4.37 (m, 1H), 4.72 (NH, d), 4.84 (d, 1H), (dd, 1H), 6.09 (d, 1H), 6.25 (s, 1H), 6.44 (d, 1H), 7.46 (m, 2H), 7.58 (m, 1H), (m, 2H).

The invention claimed is:

1. A process for the preparation of 13-(N-Boc-β-isobutylserinyl)-14-β-hydroxybaccatin III-1,14-carbonate (I)

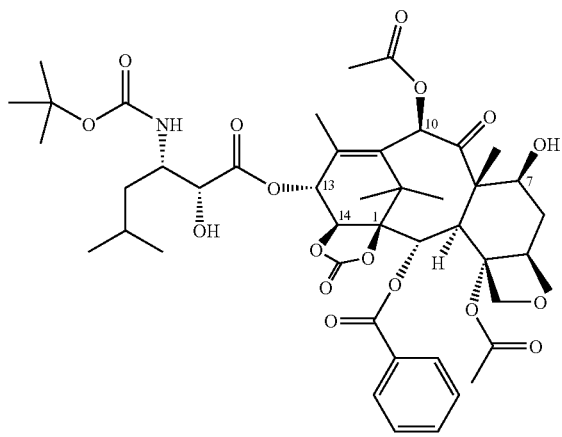

(I)

which comprises the following steps:

a) acetylation of the 10-hydroxy group of 14β-hydroxy-10-desacetylbaccatin III (IV)

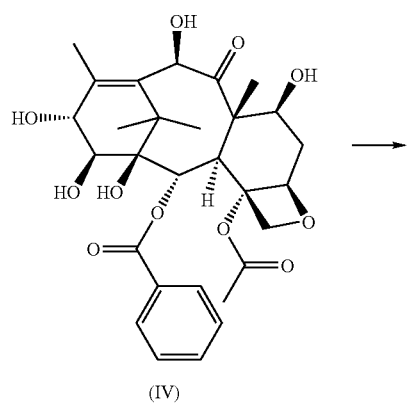

(IV)

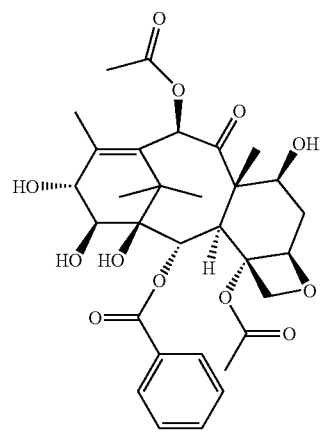

(V)

b) reaction of (V) with bis(trichloromethyl)carbonate to afford the 1,14 carbonate derivative (VI)

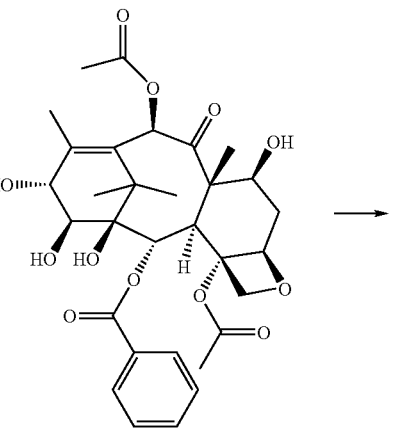

(V)

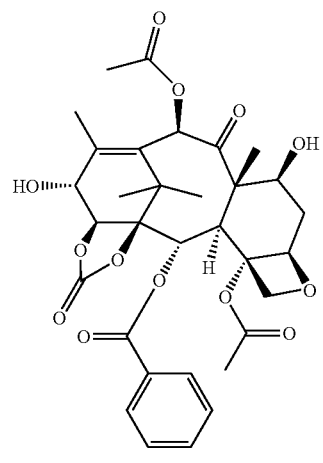

(VI)

c) reaction of (VI) with trichloroacetyl chloride to afford (VII)

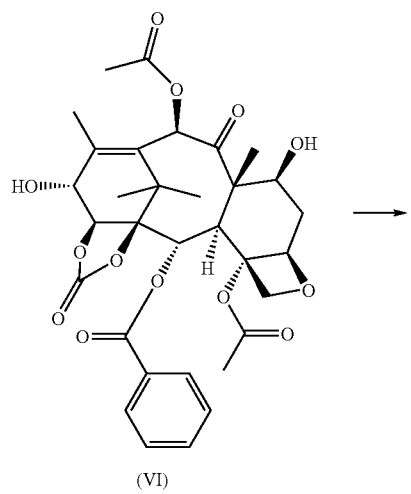
(VI)
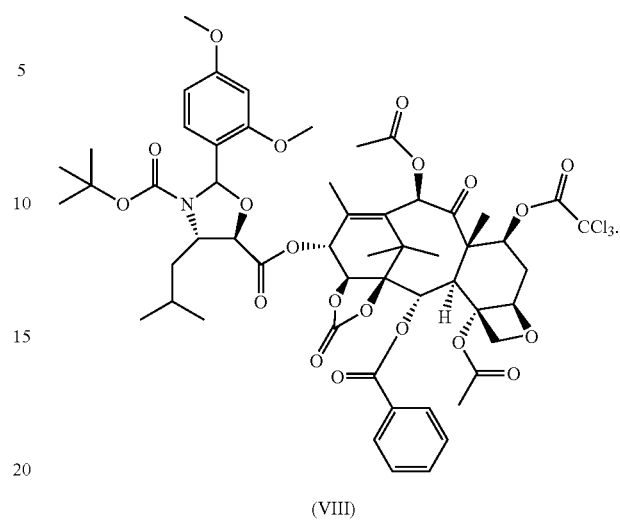
(VIII)
e) removal of the protective trichloroacetyl group with alkali from compound (VIII)
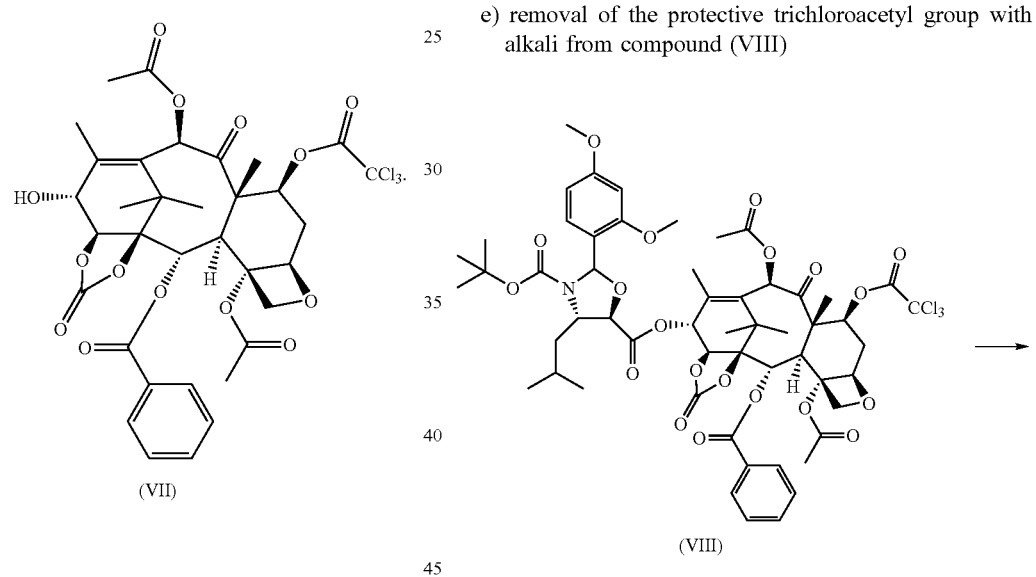
(VII)
(VIII)
d) reaction (VII) with (4S,5R)-N-Boc-2-(2,4-dimethoxyphenyl)-4-isobutyl-1-oxazolidine-5-carboxylic acid, to afford (VIII)
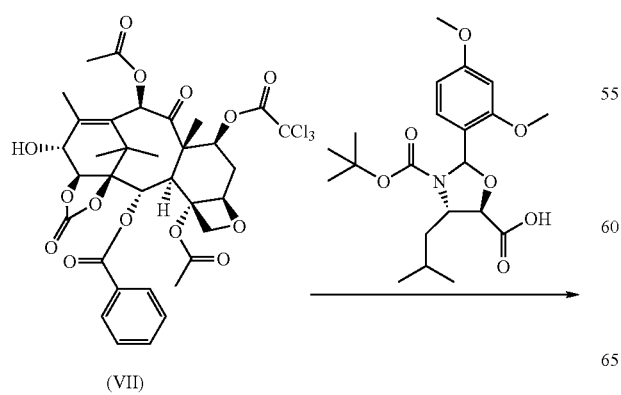
(VII)
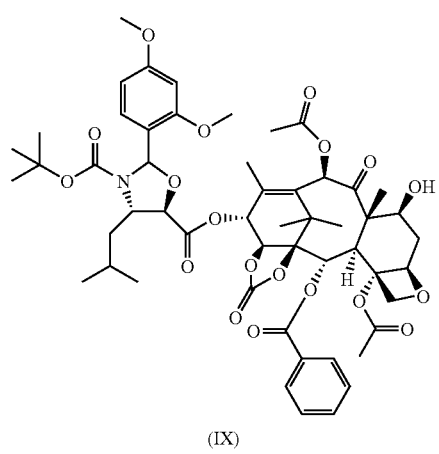
(IX)

f) removal of the dimethoxybenzylidene protective group from compound (IX)
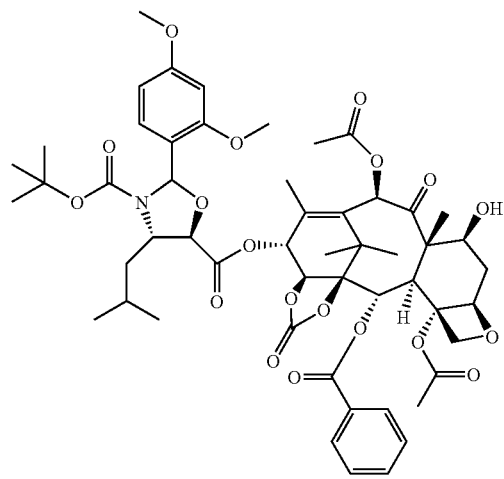
(IX)
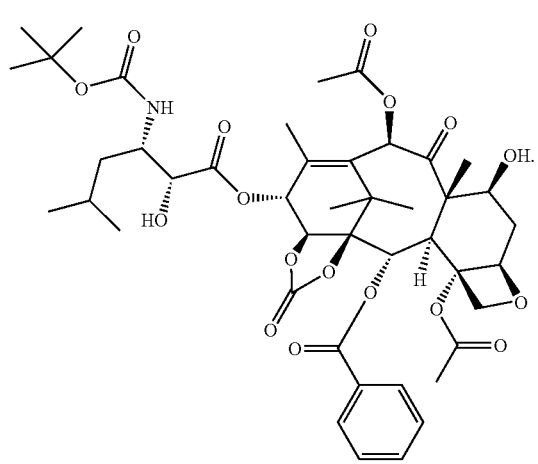
(I)
2. A compound of formula (VII):
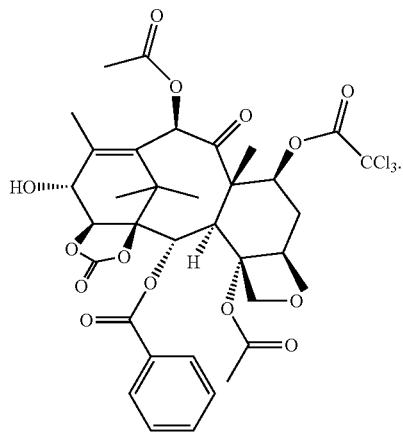
(VII)
3. A compound of formula (VIII):
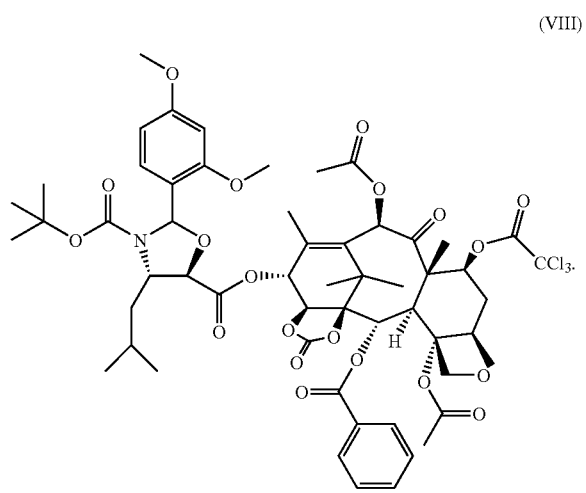
(VIII)
* * * * *